United States Patent
Colvin et al.

(10) Patent No.: US 6,512,939 B1
(45) Date of Patent: Jan. 28, 2003

(54) IMPLANTABLE ENZYME-BASED MONITORING SYSTEMS ADAPTED FOR LONG TERM USE

(75) Inventors: Michael S. Colvin, Malibu; Joseph H. Schulman, Santa Clarita; Lyle Dean Canfield, Lake Hughes; Rajiv Shah, Rancho Palos Verdes, all of CA (US)

(73) Assignee: Medtronic Minimed, Inc., Northridge, CA (US)

( * ) Notice: Subject to any disclaimer, the term of this patent is extended or adjusted under 35 U.S.C. 154(b) by 129 days.

(21) Appl. No.: 09/604,179

(22) Filed: Jun. 27, 2000

Related U.S. Application Data

(63) Continuation of application No. 08/953,817, filed on Oct. 20, 1997, now Pat. No. 6,081,736.

(51) Int. Cl.[7] ............................. A61B 5/05; A61B 5/00
(52) U.S. Cl. ........................ 600/347; 600/365; 600/377
(58) Field of Search ................................ 600/309, 345, 600/347, 365, 377

(56) References Cited

U.S. PATENT DOCUMENTS

| | | | |
|---|---|---|---|
| 4,431,004 A | 2/1984 | Bessman et al. | |
| 4,484,987 A | 11/1984 | Gough | |
| 4,627,906 A | 12/1986 | Gough | |
| 4,650,547 A | 3/1987 | Gough | |
| 4,671,288 A | 6/1987 | Gough | |
| 4,685,463 A | * 8/1987 | Williams | 600/365 |
| 4,703,756 A | 11/1987 | Gough et al. | |
| 4,721,677 A | 1/1988 | Clark, Jr. | |
| 4,759,828 A | 7/1988 | Young et al. | |
| 4,781,798 A | 11/1988 | Gough | |
| 4,890,620 A | 1/1990 | Gough | |
| 4,919,141 A | 4/1990 | Zeir et al. | |
| 5,165,407 A | 11/1992 | Wilson et al. | |
| 5,174,291 A | 12/1992 | Schoonen et al. | |
| 5,431,160 A | * 7/1995 | Wilkins | 204/403 |
| 5,497,772 A | 3/1996 | Schulman et al. | |
| 5,624,537 A | 4/1997 | Turner et al. | |
| 5,711,861 A | 1/1998 | Ward et al. | |
| 5,791,344 A | 8/1998 | Schulman et al. | |
| 5,964,993 A | * 10/1999 | Blubaugh et al. | 204/403 |
| 6,001,067 A | * 12/1999 | Shults et al. | 600/345 |

* cited by examiner

Primary Examiner—Roy D. Gibson
(74) Attorney, Agent, or Firm—Foley & Lardner

(57) ABSTRACT

Improved implantable monitoring systems suitable for long-term in vivo use to measure the concentration of one or more prescribed substances, such as glucose, are described herein. In particular, an implantable enzyme-based glucose monitoring system is described that includes at least one of the following: means for replenishing the enzyme solution as it is consumed by the enzymatic reaction; means for replenishing the electrolyte solution bathing the electrode assembly; and microprocessing means proximal the electrode assembly. In preferred embodiments, a microprocessor assembly is hermetically associated with the substrate to which the electrode assembly is affixed. Further, the monitoring systems employ one or more reservoir systems in fluid communication with enzyme and electrolyte chambers wherein the enzyme and electrolyte solutions are used. In a further embodiment, the monitoring systems use enzyme and electrolyte reservoir bulbs in fluid communication with the enzyme and electrolyte reservoirs, respectively, and positioned near the skin surface, thereby providing ready access to the enzyme and electrolyte solutions without the need for explantation of the device. Further provided herein is an enzyme solution comprising microspheres in association with the enzyme; whereby the enzyme is immobilized by the microspheres and the microspheres are in a fluid, flowable solution. Also provided herein is a method of extending the useful life of an implantable enzyme-based monitoring system, which method comprises providing means, within the system, to replenish the enzyme and/or electrolyte solution.

32 Claims, 5 Drawing Sheets

IMPLANTABLE ENZYME-BASED MONITORING SYSTEMS ADAPTED FOR LONG TERM USE

This application is a continuation application of Ser. No. 08/953,817, filed Oct. 20, 1997, now U.S. Pat. No. 6,081,736, issued Jun. 27, 2000.

BACKGROUND OF THE INVENTION

The present invention relates to implantable monitoring systems for monitoring and/or measuring biochemical substances within the body of a patient. More particularly, the present invention is directed to implantable enzyme-based monitoring systems, small enough to be implanted through the lumen of a catheter or hypodermic needle, that measure the amount and rate of change of glucose, in vivo, over an extended period of time.

Glucose is an important source of energy in the body and the sole source of energy for the brain. Glucose is stored in the body in the form of glycogen. In a healthy person, the concentration of glucose in the blood is maintained between 0.8 and 1.2 mg/ml by a variety of hormones, principally insulin and glucagon. If the blood-glucose concentration falls below this level neurological and other symptoms may result, such as hypoglycemia. Conversely, if the blood-glucose level is raised above its normal level, the condition of hyperglycemia develops, which is one of the symptoms of diabetes mellitus. The complications associated with both of these disorders, particularly if left uncorrected, can result in patient death. Thus, measuring and maintaining the concentration of glucose in the blood at a proper level is critically important for good health and longevity.

Unfortunately, some individuals are physically unable to maintain proper glucose levels in their body. For such individuals, the concentration of glucose can usually be altered, as required, to maintain health. For example, a shot of insulin can be administered to decrease the patient's glucose concentration, or conversely, glucose may be administered, either directly, as through injection or use of an intravenous (IV) solution, or indirectly, as through ingestion of certain foods or drinks.

Before a patient's glucose concentration can be properly adjusted, however, a determination must be made as to what the current glucose concentration is and whether that concentration is increasing or decreasing. Implantable glucose monitoring systems have been described that are designed to provide continuous measurement of a patient's glucose concentration. See for example, U.S. Pat. Nos. 3,539,455; 3,542,662; 4,484,987; 4,650,547; 4,671,288; 4,703,756; 4,890,620; 5,165,407; and 5,190,041. Most of these systems are based on the "enzyme electrode" principle where an enzymatic reaction, involving glucose oxidase, is combined with an electrochemical sensor, to measure either oxygen or hydrogen peroxide, and used to determine the concentration of glucose in a patient's blood. It is noted however that the implantable monitoring systems contemplated herein need not be enzyme-based; non-enzyme based (or reactant-based) monitoring systems are likewise contemplated, herein, through enzyme-based systems are preferred.

Generally, enzyme-based glucose monitoring systems, whether implantable or not, use glucose oxidase to convert glucose and oxygen to gluconic acid and hydrogen peroxide ($H_2O_2$). An electrochemical oxygen detector is then employed to measure the concentration of remaining oxygen after reaction of the glucose; thereby providing an inverse measurement of the glucose concentration. A second enzyme, catalase, is optionally included with the glucose oxidase to catalyze the decomposition of the hydrogen peroxide to water, in order to prevent interference in the measurements from the $H_2O_2$. Alternatively, an electrochemical detector capable of measuring $H_2O_2$ may be employed and from that measurement, the concentration of glucose may be determined.

The sensor assembly employed in many enzyme-based glucose monitoring systems has three basic components: an electrode assembly; an immobilized enzyme (glucose oxidase); and one or more membranes isolating these parts from one another and from the sample to be measured. See, for example, U.S. Pat. No. 4,890,620, Gough, David, issued Jan. 2, 1990; U.S. Pat. No. 4,671,288, Gough, David, issued Jan. 9, 1987; and Fischer and Abel, "A Membrane Combination for Implantable Glucose Sensors. Measurements in Undiluted Biological Fluids", *Trans. Am. Soc. Artif. Intern. Organs*, 28: 245–248 (1982), each of which is hereby incorporated by reference, in its entirety. In arranging these components, the electrode assembly may either be in direct contact with the immobilized enzyme or it may be, and preferably is, separated therefrom by a membrane. The enzyme is normally immobilized by being associated with a hydrophilic gelatinous layer composed, for example, of polyacrylamide gels, glutaraldehyde-cross-linked proteins or polyhydroxyethyl-methacrylate (PHEMA). Directly adjacent the immobilized enzyme is a hydrophobic membrane, impermeable to glucose. When contacted with the sample to be measured, oxygen diffuses into the hydrophobic outer layer and the gelatinous enzyme layer and glucose diffuses only into the gelatinous enzyme layer, thereby preventing a deficit of oxygen, which could result in an inaccurate measurement of the glucose concentration.

Two particular areas of weakness in this sensor assembly configuration, that contribute to the short life of the implantable enzyme-based glucose monitoring systems, are the finite life of the solid, immobilized enzyme layer and the finite life of the electrode assembly. Once the enzyme layer is either expended by the enzymatic reaction or inactivated by prolonged exposure to body temperatures, the entire monitoring system must be explanted and replaced. Similarly, if the electrode assembly contained within the sensor assembly ceases to function properly, for example due to pH changes at the active surface of the electrodes which may be caused by corrosion of the electrodes, again, the entire monitoring system must be replaced. Further, before the electrode assembly completely wears out, the monitoring system may require frequent recalibration to account for the assembly's deterioration. Presently, the maximum life expectancy of such monitoring systems is approximately 18 to 24 months, with recalibration required every three to six months, meaning that every couple of years, the patient must undergo surgery to remove and replace the implanted monitoring system.

Another problem with the prior art implantable glucose monitoring systems concerns their accuracy and efficiency. While the electrode assembly of these monitoring systems, which is preferably affixed to a substrate within the system, is within the patient's body, the data collected by the electrode assembly must be transmitted the length of the monitoring system's leads to the outside of the patient's body to be processed. This means the nigh impedance electrode assembly sends its weak signal a significant distance before that signal is processed. This is highly inefficient and may result in unusable and/or inaccurate readings.

Thus, what is needed are implantable monitoring systems that may remain implanted for long periods of time and that provide reliable, accurate measurements over that period of time with infrequent or no recalibrations required. Further, the monitoring system should remain as small as possible in order to maximize its usefulness as an implantable medical device.

SUMMARY OF THE INVENTION

The subject matter described and claimed herein advantageously addresses these and other needs by providing an implantable monitoring system having a microprocessor assembly associated therewith in close proximity to the electrode assembly thereof, and/or having means within the system to replenish the enzyme solution and/or electrolyte solution used therein. These improvements result in a monitoring system that is suitable for long-term in vivo use to measure the concentration of one or more prescribed substances (or analytes), such as glucose. In particular, described and claimed herein are implantable monitoring systems having one or more of the following improvements: means for replenishing the enzyme and/or other reactants as they are consumed by the enzymatic and/or other chemical reactions of the system; means for replenishing one or more reagents used within the system, particularly the electrolyte solution bathing the electrode assembly, thereby keeping the concentration of the reagent(s) constant; and signal processing means proximally associated with the electrode assembly for boosting and/or analyzing the data detected by the electrode assembly.

In preferred embodiments, a microprocessor assembly is affixed to the opposite side of the substrate upon which the electrodes-are located. The microprocessor assembly is hermetically sealed on the substrate by, for example, covering the assembly with a metal can which is heat bonded to the substrate. Hermetic feed-throughs within the substrate electrically connect the electrode assembly to the microprocessor assembly, thereby quickly and efficiently transmitting the data collected by the electrode assembly to the microprocessor assembly. This configuration permits the high impedance electrode assembly to send its weak signal only a very short, well insulated distance to the microprocessor attached to the substrate. The microprocessor assembly then boosts the received signal, for example, by digitizing it before sending it out over the monitoring system leads.

In further preferred embodiments, a reservoir of reactant solution, in fluid communication with a reaction chamber located proximate the working electrode of the sensor assembly, is employed to provide a constant supply of unused reactant solution to the sensor assembly. Most preferably the reactant solution comprises an enzyme solution and the monitoring system is an enzyme-based one. Similarly, preferred embodiments described and claimed herein, employ a reagent reservoir system to provide a constant supply of reagent(s) to the monitoring system. In particular, an electrolyte solution is used to bathe the electrodes of the sensor assembly. Thus, an electrolyte reservoir system is employed to provide a constant supply of electrolyte solution to the electrodes, thereby extending the useful life of the electrolyte by, for example, diluting the by-products of electrode corrosion, and thus maintaining the pH of the environment of the electrodes.

Further provided herein is an enzyme solution comprising polymer microspheres in association with a prescribed enzyme, such as glucose oxidase. Association of the prescribed enzyme with the microspheres advantageously maintains a desired enzyme concentration, prevents leakage of the enzyme from the sensor assembly and increases the longevity, reliability and accuracy of the enzyme-based monitoring system.

Also provided herein is a method of extending the useful life of an implantable monitoring system, which method comprises providing means, within the system, to replenish the reactant and/or reagent solutions, particularly enzyme and electrolyte solutions.

These and other objects, features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

In the following detailed description, reference will be made to the attached drawings in which.

The numbering between Figures is consistent, such that the same item illustrated in more than one Figure bears the same identifying number in each Figure.

DETAILED DESCRIPTION OF THE PREFERRED EMBODIMENTS

The following description is of the best mode presently contemplated for carrying out the invention. For example, the description is directed to an enzyme-based glucose monitoring system. It will be appreciated by those of skill in the art that the improvements described herein are useful for monitoring systems designed to measure substances other than or in addition to glucose as well as for enzyme-based and non-enzyme-based monitoring systems. Thus, this description is not to be taken in a limiting sense, but is made merely for the purpose of describing the general principles of the invention and preferred embodiments thereof. The scope of the invention should be determined with reference to the claims.

Definitions

The most preferred embodiments described herein are enzyme-based glucose monitoring systems employing an electrolyte solution to bathe the electrodes of the sensor assembly within the system. Therefore, throughout the description, terms such as "enzyme-based," "enzyme reservoir," "enzyme chamber," "enzyme channel" and "enzyme solution" are used. As used herein, each of these terms are considered synonymous with "reactant-based," "reactant reservoir," "reactant chamber," and "reactant channel," respectively.

Similarly, the most preferred monitoring-system embodiments described herein employ an electrolyte solution to bathe the electrodes of the sensor assembly. However, it may be desirable to use one or more other reagents either in addition to or in place of such an electrolyte solution. Thus, terms such as "electrolyte solution," "electrolyte reservoir," "electrolyte chamber" and "electrolyte channel," as used herein, are considered synonymous with "reagent solution," "reagent reservoir," "reagent chamber" and "reagent channel," respectively.

Figure 1:
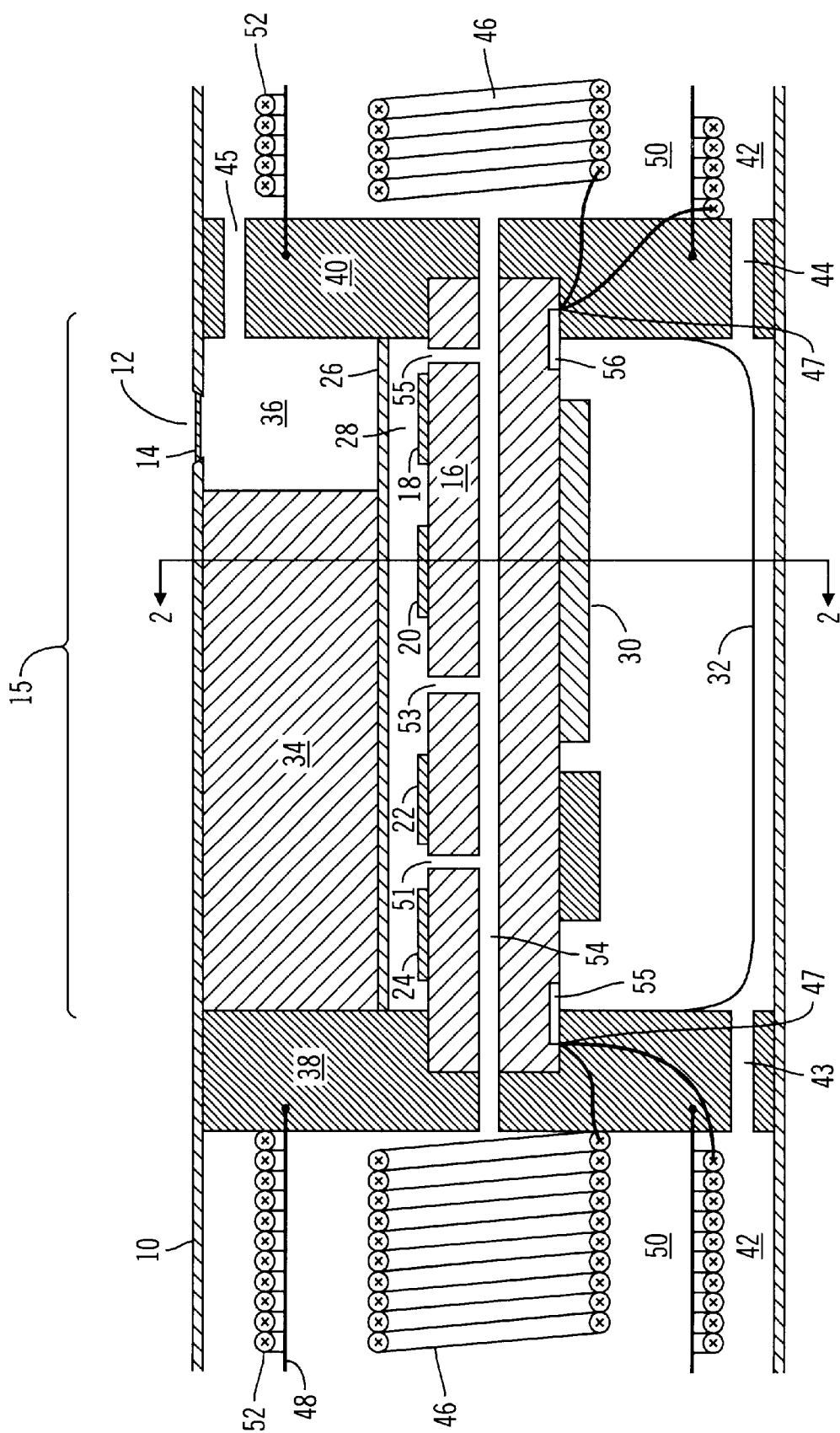
FIG. 1 is a side view of a preferred embodiment of the implantable monitoring system in accordance with the present invention.

As used herein, the term sensor assembly refers to that portion of the monitoring system that is directly involved in sensing the concentration of the substance(s) being measured, that is the substrate and associated electronics, membranes, enzyme(s), and/or solutions. A monitoring system, as contemplated herein, may, and preferably does, include more than one sensor assembly. Additionally, each sensor assembly includes the microprocessor assembly, where such is present. A single sensor assembly, including microprocessor assembly, is identified in FIG. 1 by reference number 15. Although the epoxy plugs 38, 40 shown in FIG. 1 are not part of the sensor assembly as defined herein, they or their functional equivalents will be associated with each sensor assembly within the preferred monitoring system contemplated herein.

As used herein, the term electrode assembly refers to the electrodes employed by a single sensor assembly to detect in vivo substance concentrations and the electronic connections between the electrodes. Each electrode assembly has an active surface and an inactive surface. The active surface of the electrode assembly is that face that is exposed to the substances being measured. In contrast, the inactive surface of the assembly is that face that is affixed to the substrate of the sensor assembly. It will be appreciated that the active and inactive surfaces of the electrode assembly corresponds to active and inactive surfaces of the individual electrodes comprising the assembly.

As used herein, the term detection apparatus refers to the electrode assembly, the substrate to which the electrode assembly is bonded, the membrane means surrounding the electrodes and forming the electrolyte chamber, the microprocessor assembly associated with the substrate and the lead system.

As used herein, the term microprocessor assembly refers to the microprocessor chip and associated microelectronics that are affixed to the same substrate as the electrode assembly and that function, at least, to receive and process data from the electrodes. Such microprocessor assemblies are described in detail in the following co-pending applications: "Low Power Rectifier Circuit for Implantable Medical Device," U.S. Ser. No. 08/928,871, now U.S. Pat. No. 5,999,849, issued Dec. 7, 1999; "Low Power Current to Frequency Converter Circuit for Use in Implantable Sensors," U.S. Ser. No. 08/928,868, now U.S. Pat. No. 5,917,346, issued Jun. 29, 1999; and "Daisy-Chainable Sensors and Stimulators for Implantation in Living Tissue," U.S. Ser. No. 08/928,867, now U.S. Pat. No. 5,999,848, issued Dec. 7, 1999, each of which is incorporated herein in its entirety.

As used herein, the term command center refers to a computer unit, external and/or internal to the patient, that provides power to and controls the operation of the monitoring system. The functions of the command center may be divided between an internal unit and an external unit. For example, the internal unit may be capable of providing the necessary power to operate the monitoring system and sufficient memory to record the data received from the one or more sensor assemblies comprising the monitoring system, and the external unit may be capable of retrieving the stored data from the internal unit and processing it to provide the desired specific information. An example of a command center useful herein is discussed in U.S. Pat. No. 5,497,772, Schulman, et al., which patent is incorporated in its entirety by reference herein.

It is noted that use herein of the terms hydrophobic and hydrophilic to refer to membranes employed by the monitoring systems should not be considered limiting, but are used only to facilitate reading the present description. What is important is that the membranes be selectively permeable; for example, a membrane covering an electrode should be selectively permeable for those ions that are to be detected by the electrode (such as oxygen) and impermeable to substances that would interfere with that detection (such as glucose). Similarly, membranes covering the enzyme of the enzyme-based system should be permeable to the enzyme reactants (such as glucose and oxygen) and impermeable to substances that could interfere with the enzymatic reaction. Thus, it will be appreciated by those of skill in the art that various alternative embodiments of the present invention are contemplated herein.

The improvements described and claimed herein are useful for any implantable monitoring system that employs or could employ a fluid solution within the system. In particular, where operation of the implantable monitoring system entails exhaustion and/or possible contamination of a fluid solution over time, the improvements claimed herein will prolong the useful life of the monitoring system and improve its operation by providing means for replenishing one or more fluid solutions contained in the system. In particular, the improved system described herein includes reservoirs, containing fresh/unused fluid solution, connected via channels to chambers, within which the fluid solutions are used or may become contaminated. This configuration thereby permits the free flow of the fluid solution, fresh and used, in and out of the chambers within which they are used.

Further, the improved configuration described and claimed herein, having a microprocessor assembly in very close proximity to the electrode assembly, is also useful for almost any implantable monitoring system. Even monitoring systems that do not employ any fluid solutions will benefit from this improvement, as it dramatically improves the accuracy and reliability of monitoring systems by requiring the high impedance electrodes to transmit their weak signal only a short distance to the microprocessor where the signal is then digitized or otherwise boosted and sent to the glucose pump and/or command center.

DESCRIPTION OF PREFERRED EMBODIMENTS

Turning now to FIG. 1, there is shown a side view of a preferred embodiment of the monitoring system in accordance with the present invention. Specifically, illustrated is an implantable enzyme-based glucose monitoring system according to the present in invention. The basic configuration of the monitoring system is a substrate 16 having electrodes 18, 20, 22, 24 bonded thereto, surrounded by a selectively permeable membrane 26 within which an electrolyte solution is contained, an enzyme located near a first working electrode, a selectively permeable membrane located near the remaining electrodes and a selectively permeable, biocompatible housing surrounding all. Also illustrated in FIG. 1 is the improved configuration of a microprocessor assembly 30 affixed to the same substrate as the electrode assembly. This is described further below and in the following co-pending applications: "Low Power Rectifier Circuit for Implantable Medical Device," U.S. Ser. No. 08/928,871, now U.S. Pat. No. 5,999,849, issued Dec. 7, 1999; "Low Power Current to Frequency Converter Circuit for Use in Implantable Sensors," U.S. Ser. No. 08/928,868, now U.S. Pat. No. 5,917,346, issued Jun. 29, 1999; and "Daisy-Chainable Sensors and Stimulators for Implantation in Living Tissue," U.S. Ser. No. 08/928,867, now U.S. Pat. No. 5,999,848, issued Dec. 7, 1999, each of which has previously been incorporated herein in its entirety. It will be appreciated by those of skill in the art that there are many specific configurations the monitoring system can possess, each of which are likewise contemplated herein.

One alternative configuration contemplated herein comprises two monitoring systems, each having a single sensor assembly, wherein one of the monitoring systems employs an enzyme-based sensor to measure a substance of interest and the second system measures concentrations of a background substance. Thus, for example, where the two monitoring systems are designed to measure glucose concentrations, one of the systems may employ glucose oxidase and an oxygen sensor to measure remaining oxygen after exhaustion of glucose in the enzymatic reaction, and the second system may comprise an oxygen sensor without any associated enzyme, the second system measuring background oxygen concentrations. Additional configurations will be apparent to those of skill in the art and are likewise contemplated herein.

Referring now to FIG. 1, a housing 10 forms the exterior of the monitoring system and is the portion that comes in direct contact with the internal environment of the patient, hence the need for biocompatibility. Most preferably the exterior surface of the monitoring system is coated or otherwise treated to prevent blood coagulation and/or tissue growth thereon, as described, for example, in co-pending application entitled "Implantable Enzyme-Based Monitoring Systems Having Improved Longevity Due To Improved Exterior Surfaces," Schulman, et al., U.S. Ser. No. 08/954,166, now U.S. Pat. No. 6,119,028, issued Oct. 12, 2000, which application is hereby incorporated by reference, in its entirety.

For the purposes of monitoring in vivo glucose concentrations, the housing is preferably formed of a flexible, oxygen permeable material such as silicone rubber. To optimize operation of this particular embodiment, the housing is preferably impermeable to glucose. An opening 12 is formed within the housing, through which the glucose will pass. The opening 12 is preferably covered by a polymeric glucose-permeable-membrane means 14, such as 2-hydroxyethyl methacrylate (HEMA), porous or perforated polydimethylsiloxane, or similar material. The membrane 14 is adhered to the housing, thereby providing a fully covered opening within the housing. Examples of suitable housing, opening and membrane covering configurations may be found in co-pending patent application entitled "Implantable Enzyme-Based Monitoring Systems Having Improved Longevity Due To Improved Exterior Surfaces," Schulman, et al., U.S. Ser. No. 08/954,166, now U.S. Pat. No. 6,119,028, issued Oct. 12, 2000; U.S. Pat. No. 4,671,288, Gough, D., issued Jun. 9, 1987 and U.S. Pat. No. 5,165,407, Wilson, et al., issued Nov. 24, 1992, each of which is hereby incorporated by reference, in its entirety.

Positioned within the housing 10 is a substrate 16. The substrate 16 may be formed of any suitable material as is well known in the art; for example, preferred substrate materials include ceramic, glass and other non-conductive, electrically insulated materials. Preferably, the substrate 16 is elongated and is positioned within the housing 10 such that one end is proximate the covered opening 12 of the housing. Bonded to one side of the substrate is the electrode assembly. In the preferred embodiment illustrated herein, four electrodes; a first working electrode 18, reference electrode 20, counter electrode 22 and second working electrode 24, and the electrical connections associated therewith, comprise the electrode assembly. For an example of an appropriate configuration of the electrode assembly, including descriptions of the electrodes and metalized traces therebetween that may be employed, see U.S. Pat. No. 5,497,772, Schulman, et al., incorporated in its entirety by reference herein.

The first and second working electrodes 18, 24, respectively, are preferably spaced furthest from each other relative to their distance from the other two electrodes. This is in done in order to prevent interference in the measurements taken by each working electrode from the substances being measured by the other working electrode. The reference electrode 20 and counter electrode 22, then, are preferably positioned between the two working electrodes, as illustrated in FIG. 1. Further, the first working electrode 18 is preferably positioned on the substrate at a point adjacent the opening 12 in the housing with the enzyme chamber 36 therebetween. This too is shown in FIG. 1. In this preferred embodiment, both working electrodes measure oxygen concentration; the first measuring remaining oxygen after exhaustion of glucose and necessary oxygen in the enzymatic reaction and the second measuring total (background) oxygen concentrations.

Surrounding the electrode assembly and covering the face of the substrate upon which the electrode assembly is affixed, is a first membrane means 26. The first membrane means 26 forms an electrolyte chamber 28 within which an electrolyte solution (or similar conductive fluid) is located. The electrolyte solution serves to bathe the electrode assembly thereby extending the life thereof. In a preferred embodiment, the electrolyte chamber 28 is filled with a gelatinous material (gel matrix), such as polyhydroxyethylmethacrylate (PHEMA). The gelatinous material is "soaked" with an electrolyte solution and serves to support the membrane 26 covering the electrodes. In this embodiment, the electrolyte channels 54, 51, 53 and 55, located within the substrate, do not contain the gel matrix. Because the gel matrix is slow to exchange fluid, more than one electrolyte channel 51, 53 and 55 connecting to the electrolyte chamber 28 is preferred, thereby facilitating flow and mixing of the electrolyte. While three such channels are illustrated, it will be appreciated that more or less than three may be employed, as long as the electrolyte solution is able to flow throughout the electrolyte chamber.

Adjacent the first membrane means 26 and filling the space between the exterior housing 10 and that portion of the first membrane means 26 over the second working, reference and counter electrodes, is a hydrophobic membrane means 34, which is permeable to oxygen and impermeable to glucose. In the preferred embodiment illustrated, the substrate 16 is held in position within the housing 10 by two plugs 38, 40, preferably formed of epoxy or a similar material. The plugs 38, 40 are preferably located at either end of the elongated substrate, grip the substrate ends and form a seal within the housing 10, thus isolating the entire sensor assembly 15 from the rest of the monitoring system, except where channels are employed within the plugs, as discussed further below. An important function of the plugs 38 and 40 is to provide insulation for the wire-pad connections from the leads 46 and 52 to the lead pads 47.

As illustrated in FIG. 1, in this preferred embodiment, an enzyme chamber 36 is formed by the epoxy plug 40, located at the end of the elongated substrate 16 near the first working electrode 18; the hydrophobic oxygen permeable membrane means 34, filling the space between the first membrane means 26 over the remaining electrodes 20, 22, 24 and the housing 10; the first membrane means 26 over the first working electrode 18; and the housing 10 with opening 12 covered by membrane means 14. The enzyme is located within the enzyme chamber 36 and may be an immobilized enzyme solution, as known in the art, or may be a fluid enzyme solution, as described below, or both. Examples of immobilized enzyme solutions, particularly immobilized glucose oxidase solutions suitable for use in an implantable monitoring system, are described in U.S. Pat. No. 4,890,620, Gough, David; U.S. Pat. No. 4,671,288 Gough, David; U.S. Pat. No. 3,948,745, Guilbault, et al.; and U.S. Pat. No. 4,759,828 Young, et al., each of which is incorporated herein, in its entirety.

As stated above, in this preferred monitoring system embodiment, a microprocessor assembly is hermetically associated with the substrate. The microprocessor assembly comprises integrated circuits and microelectronics 30 used to process the electrical signals created at the electrodes and to process data received from the command center. The microprocessor assembly may be hermetically associated with the substrate by any of a number of known means by those of skill in the implantable medical device art. For example, the hermetic seal may be formed by braising a metal, such as stainless steel, lid or can 32 onto the substrate covering the microprocessor assembly. The can 32 may occupy nearly all of the space between the substrate 16, the housing 10 and the plugs 38, 40. If such is the case, then a dimple (not shown) may be formed in the can to permit passage of the enzyme solution about the can.

In operation, glucose diffuses through the polymeric glucose-permeable membrane means 14 and enters the enzyme chamber 36. oxygen diffuses through both the membrane means 14 and the housing 10 into the enzyme chamber and into and through the hydrophobic membrane means 34. Within the enzyme chamber 36, glucose and oxygen react in the presence of the enzyme, glucose oxidase, to form gluconic acid and hydrogen peroxide. A second enzyme, catalase, is optionally included with the glucose oxidase in the enzyme chamber. Catalase catalyzes the decomposition of hydrogen peroxide to water and may be useful to prevent interference from hydrogen peroxide in the measurement of oxygen by the first working electrode 18. Because oxygen has better access to the enzyme chamber 36 than does glucose, glucose is the limiting reagent in the enzymatic reaction. Thus, the first working electrode 18 measures the amount of oxygen remaining after exhaustion of glucose by the enzymatic reaction.

Simultaneous with operation of the first working electrode, the second working electrode 24, measures the total unreacted oxygen concentration thereby providing a background oxygen measurement from which the measurement taken by the first electrode may be subtracted. Feedthroughs between the electrodes and chip assembly, illustrated for example in FIG. 2 as item 57, permit the chip assembly to process the signals detected by the electrode assembly. Leads 44, 52 which are in electrical contact with the chip assembly via one or more feed-throughs, permit bidirectional transport of information between the chip assembly and the command center. The electronic operation of the monitoring system is preferably as is described in U.S. Pat. No. 5,497,772, Schulman, et al, incorporated herein, in its entirety, by reference.

Further, as previously stated, the monitoring system preferably comprises more than one, particularly about six, sensor assemblies in a daisy chain configuration. Thus, the leads 46, 52, preferably extend between sensor assemblies as well as between the first sensor assembly and the command center and/or glucose pump. Such daisy-chainable sensors are described in detail in "Daisy-Chainable Sensors and Stimulators for Implantation in Living Tissue," Shulman, et al., filed Sep. 12, 1997, U.S. Ser. No. 08/928,867, now U.S. Pat. No. 5,999,848, issued Dec. 7, 1999, which has previously been incorporated by reference, in its entirety.

In the preferred embodiment, illustrated in FIG. 1, the leads 46, 52 are shown as coaxial. For the sake of maximizing use of the available space, this general configuration is preferred. As illustrated, the inner lead 46 is coiled within an inner housing means 48. The inner housing means 48 is preferably formed of a flexible electrically non-conductive material such as silicone rubber, TEFLON, manufactured by DuPont Company, or similar material and preferably is formed of silicone rubber. Coiled around the exterior surface of the inner housing means 48 is the outer lead 52. Each lead 46, 52 is also electrically isolated from its immediate external environment, for example, by being individually coated with a non-conductive insulating material, such as and preferably TEFLON.

Figure 5:
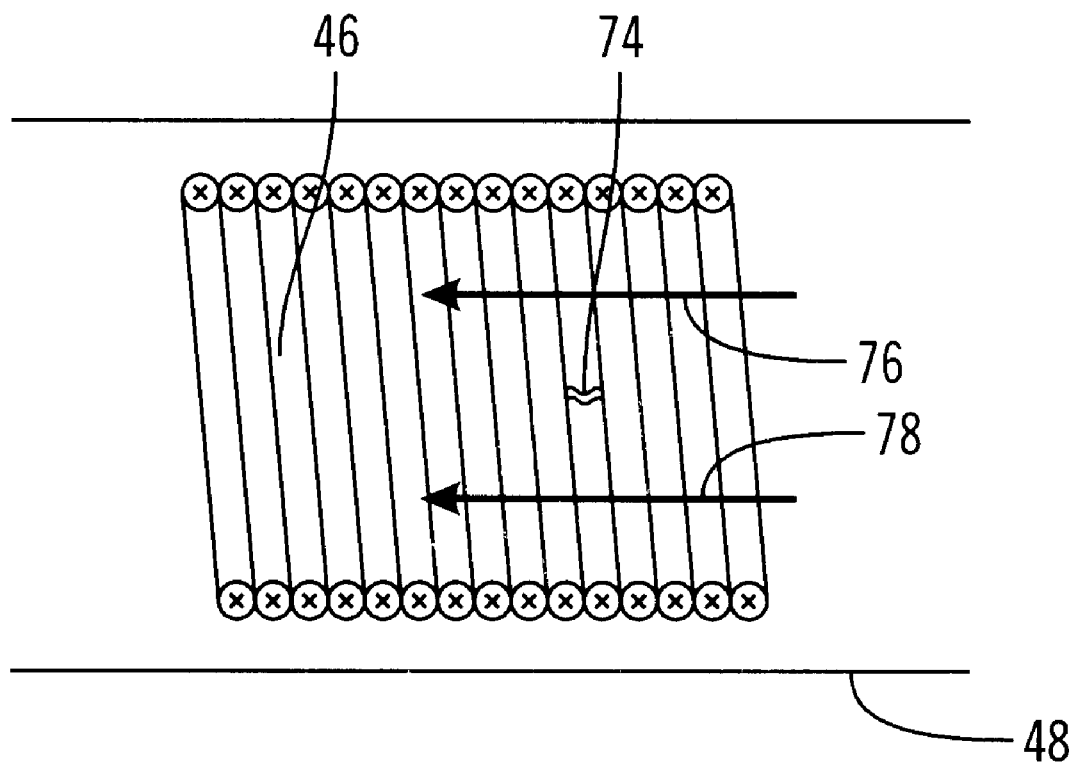
FIG. 5 is a side view of one of the leads of the monitoring system illustrating an advantageous configuration thereof.

Alternatively to coating each lead individually in order to electrically isolate it from its immediate external environment, the lead may be coiled within an insulating material as in a sleeve of TEFLON or silicone rubber. It is noted that tightly coiling a lead against itself with an insulating sleeve may advantageously prolong the life of the lead by providing alternative electrical pathways in the event the lead breaks in a particular location. This is illustrated in FIG. 5 wherein a lead 46 is shown cut at a single location 74 with exemplary alternative electrical pathways shown as 76 and 78. Thus, the leads 46, 52 should be electrically isolated both from one another and from their immediate external environment, though not necessarily from themselves.

The inner housing means 48 is tightly associated with the epoxy plugs 38, 40 such that there is no communication between the inner portion of the inner housing means 48 and the inner portion of the outer housing means 10. The inner housing means 48 may be imbedded within the epoxy plugs 38, 40, for example by forming a compression seal around a bulbed end of the inner housing means, in order to provide the tight association or may be otherwise associated with or affixed to the epoxy plugs 38, 40.

Thus, in this preferred embodiment, the inner housing means 48, forms an electrolyte reservoir within which an electrolyte solution is stored. An electrolyte channel 54 is formed within the substrate and is in fluid communication with both the electrolyte reservoir 50 and the electrolyte chamber 28. In operation, the electrolyte solution within the monitoring system is in constant flux between the electrolyte chamber 28, electrolyte channels 54, 51, 53, 55 and electrolyte reservoir 50; thereby providing a constant supply of fresh electrolyte solution to the electrodes and extending the useful life of the system by, for example, helping to maintain a constant pH around the electrodes. Further, where the monitoring system comprises more than one sensor assembly 15, as previously described, the electrolyte solution moves throughout all such sensor assemblies, providing constant replenishment of electrolyte solution to each sensor assembly. Any suitable conductive fluid, as is well known in the art, will be suitable for use as an electrolyte solution; for example, a saline solution.

In addition to the electrolyte reservoir 50, an enzyme reservoir 42 is formed by the outer surface of the inner housing means 48 and the inner surface of the outer housing 10. Thus, the outer lead 52 is within the enzyme chamber 42, though electrically isolated therefrom. The enzyme solution is contained within the enzyme reservoir 42. Each epoxy plug 38, 40 has an enzyme channel 43, 44 therethrough. In the preferred embodiment illustrated, the enzyme channels are located to provide fluid communication between the enzyme reservoir and the area beyond where the chip assembly is hermetically sealed to the substrate. Additionally, an enzyme channel is formed within the opposite end of one epoxy plug 40 to provide access to the enzyme chamber 36. Thus, in operation, the enzyme solution is able to move freely between the enzyme reservoir, enzyme channels and enzyme chamber; thereby providing a constant supply of fresh enzyme to the enzyme chamber and extending the useful life of the monitoring system. Further, where more than one sensor assembly 15 is employed in the monitoring system, the enzyme solution is able to flow between the sensor assemblies replenishing the supply of active enzyme for each.

As discussed briefly above, methods of immobilization of the enzyme solution within the enzyme chamber are well known in the art. For example, the enzyme may be contained within or associated with a gelatinous material, such as polyacrylamide gels, glutaraldehyde, cross-linked collagen or albumin, poly-hydroxyethylmethacrylate (PHEMA) and its derivative and other hydrophilic polymers and co-polymers. For the purposes herein, the term enzyme solution refers to gelatinous as well as fluid compounds comprising the enzyme of interest. Preferably, where a gelatinous enzyme is immobilized in the enzyme chamber, a fluid enzyme solution is contained within the enzyme reservoir and channels; thereby permitting the fluid enzyme solution to flow from the enzyme reservoir into the enzyme chamber as the gelatinous enzyme is expended.

In a most preferred embodiment, the fluid enzyme solution, whether used in conjunction with the gelatinous enzyme solution or used as the sole source of enzyme, is comprised of microspheres having enzyme molecules associated therewith. Microspheres, i.e. microspherical polymers, have been used in chromatography columns for years and thus are readily available commercially from, for example, Bang Laboratories, Inc., Carmel, Ind. Because the microspheres are isolated within the monitoring system, they will not enter the body of the patient and will pose little threat to the individual.

Various types of microspheres are known; for example, polystyrene, styrene/persulphate polymers, polyacrylamide, and beaded agarose. Beads may range in size from $0.01\ \mu M$ to more than $10\ \mu M$ in diameter and will have differing pore sizes depending, in part, upon the material from which they are constructed and their overall diameter. Microspheres may be formed of hydrophilic or hydrophobic materials, and the compounds associated therewith may be ionically or covalently bound within and/or without the beads. Thus, in operation, the microspheres serve to immobilize the enzyme on, in or near the microsphere while permitting the solution as a whole to remain fluid.

For the purposes herein, either hydrophilic or hydrophobic microspheres may be employed in association with the enzyme; however, microspheres formed of hydrophilic material are preferred where the substrate of the enzyme is glucose, such as in the preferred embodiments illustrated herein, as they will be most permeable to glucose. The bead size should be selected to be large enough not to permeate the second membrane means 14 covering the opening 12 within the housing 10, but small enough to move freely within the monitoring system, that is through and between the enzyme reservoir, enzyme channels and enzyme chamber. For example, preferred herein are mixtures of beads of relatively homogenous size, ranging from about $0.02\ \mu M$ to about $10\ \mu M$, and more preferably from about $0.02\ \mu M$ to about $5\ \mu M$. Also preferred herein is a covalent association of the enzyme with the microspheres. Covalent binding of the enzyme insures proper presentation of the enzyme's active site and, therefore, increases the efficiency of the enzyme solution. It is noted that, depending upon the type and size of microsphere employed, use of a spacer arm between the enzyme and microsphere may be preferred. Spacer arms are molecules, generally small molecules, used to space the enzyme from the microsphere and/or to provide a stronger covalent association between the enzyme and microsphere. For examples of detailed descriptions of the construction of microspheres and conjugation of molecules thereto, see van Oss, C. J. and Singer, J. M., *J. Reticuloend. Soc.* 3: 29–40 (1966); Menger, F. M. and Tsuno, T., *J. Am. Chem. Soc.* 112: 6723–24 (1990); Ugelsgtad, J., et al., *Adv. Colloid Interface Sci.*, 13: 101–140 (1980); and Ugelstad, J., et al., *Makromolec. Chem.* 180: 737–744 (1979), each of which is incorporated herein, in its entirety. Examples of microspheres preferred for use herein include polystyrenes and styrene/persulphate polymers.

In preferred embodiments, the enzyme concentration ranges from about 1 molar percent to as much as 50 molar percent of the enzyme solution, and the microspheres are in an aqueous buffered solution, such as a phosphate saline solution. It will be readily appreciated by those of skill in the art that the specifics of the microspheres employed in the monitoring system described herein may vary widely. This is because the primary function of the microspheres is to immobilize the enzyme within a fluid solution in order to permit movement of exhausted enzyme out of the enzyme chamber and movement of active enzyme into the enzyme chamber.

The enzyme solution employed herein may comprise one or more enzymes and may additionally include co-factors necessary for the enzymatic reaction. For example, where glucose is the substance of interest, as in the presently preferred embodiments, glucose oxidase may be used to convert the glucose, in the presence of molecular oxygen, to gluconic acid and hydrogen peroxide. Optionally, and preferably, a second enzyme, catalase, is included in the enzyme solution. Catalase catalyzes the decomposition of hydrogen peroxide, thereby preventing it from interfering with measurements made by the electrochemical oxygen sensor. It will be appreciated by those of skill in the art that additional enzymes and/or co-factors may be included in the enzyme solution. Preferably, where microspheres are employed, all enzymes and co-factors are associated with the microspheres. Each microsphere may have one or more than one type of enzyme and/or co-factor associated therewith.

Figure 6:
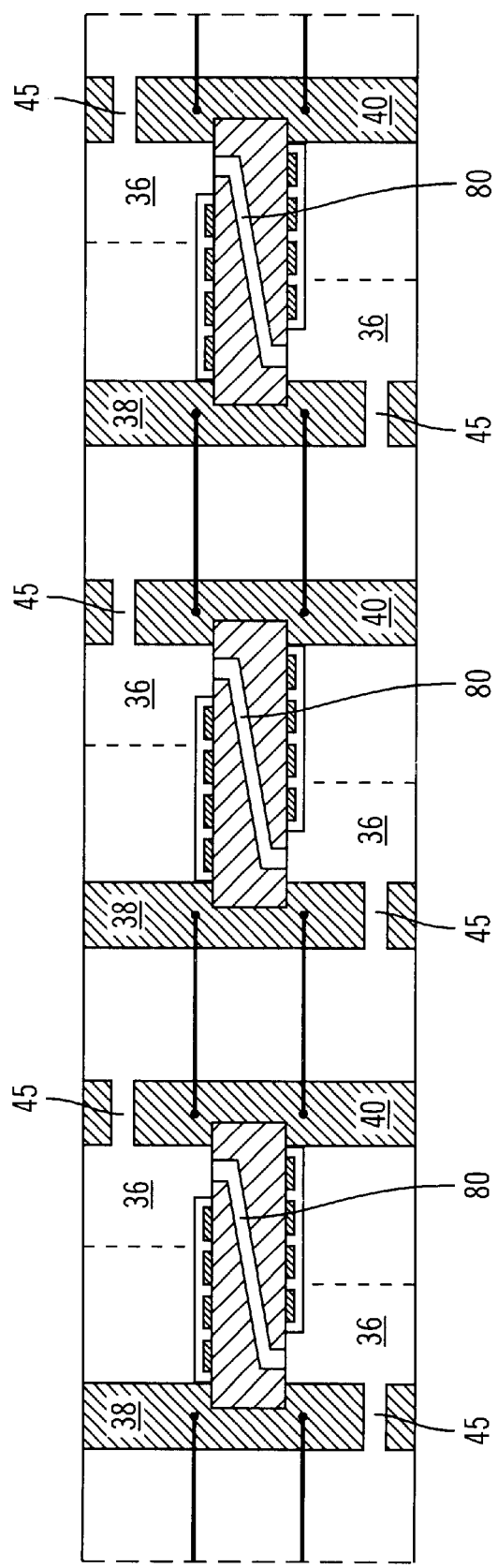
FIG. 6 is a side view of an alternative embodiment of the improved monitoring system illustrating double sensor assemblies and a modified enzyme reservoir system.

Alternatives to the specific reservoir systems and lead configurations described above and illustrated in FIGS. 1, 2 and 4 will be readily appreciated by those of skill in the art. One such alternative contemplated herein is illustrated in FIG. 6. This alternative configuration employs two electrode assemblies affixed to a single substrate (one on either side) with the microprocessor assembly eliminated or placed within the substrate. In such an alternative embodiment, the enzyme and electrolyte reservoirs and channels, if any, would require modification in order to permit the flow of enzyme and electrolyte solution around both electrode assemblies in an appropriate manner. In FIG. 6, only the basic configuration of the dual sensor assemblies and modified enzyme reservoir system are detailed. It will be appreciated that a lead system, electrolyte reservoir system and membrane systems are also present, though not detailed in the figure. Further, the configuration illustrated in FIG. 6 is susceptible to use either with the microprocessor assembly centered in the substrate, which is preferable, or with the microprocessor assembly exterior to the sensor assembly.

Turning then to FIG. 6, a preferred embodiment of the double sensor alternative configuration is shown, wherein the electrode assemblies on a single substrate are positioned opposite one another rather than as mirror images. In this configuration, one enzyme channel 45 through each epoxy plug 38, 40 would connect a single enzyme chamber 36 to the enzyme reservoir 42 (see FIG. 1) and a single enzyme channel 80 through the substrate would connect the two enzyme chambers 36 associated with a single substrate. In FIG. 6, three double sensor assemblies are shown to illustrate the interconnectedness of the enzyme reservoir system. Not illustrated in FIG. 6, but implied by the basic configuration is the addition of one or more electrolyte channels to the substrate to provide electrolyte solution to the electrode assembly on each side of the substrate.

As with the alternative reservoir system shown in FIG. 6, the lead system described above and illustrated in FIGS. 1, 3 and 4 may be modified without compromise to the general improvements described herein. Thus, the leads 46, 52 of the monitoring system may be positioned almost anywhere within the housing 10, as long as they are electrically isolated from one another and from their exterior surroundings, for example by coating with a waterproof, pinhole-free insulation material such as TEFLON. Therefore, both leads 46, 52 may be housed within or both without the inner housing means 48 and may be coaxial or not. All such alternatives are contemplated herein. It is noted that in addition to the need for electrical isolation of the leads, the enzyme reservoir and electrolyte reservoir must be isolated from one another, in order to prevent contamination of the solutions contained therein.

Figure 2:
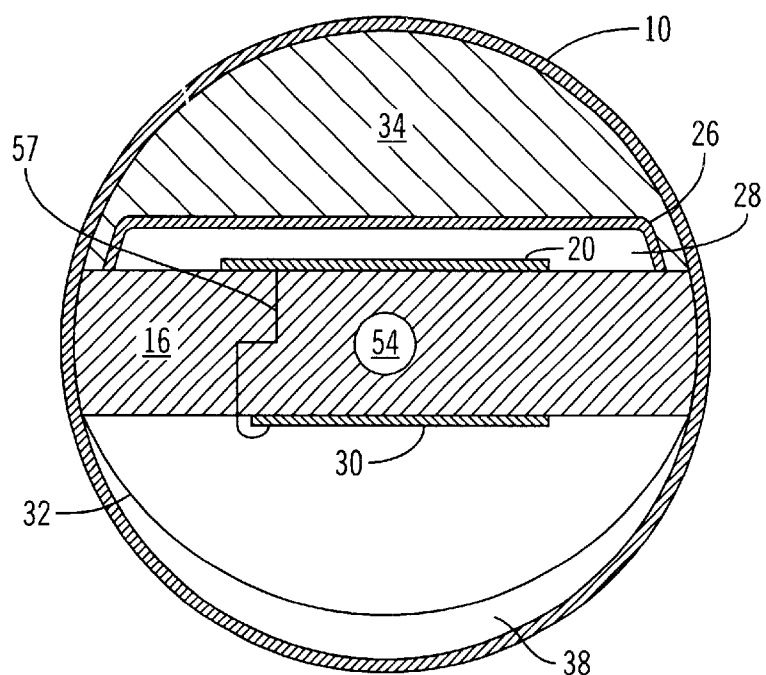
FIG. 2 is a cross-sectional view of the implantable monitoring system of FIG. 1 taken along the line 2–2'.

FIG. 2 is a cross-sectional view, taken along the line 2–2', of the monitoring system illustrated in FIG. 1. This Figure shows how, in this preferred embodiment, the substrate 16, extends (in the horizontal direction as illustrated) to contact the walls of the housing 10. In conjunction with the epoxy plugs 38, 40, the substrate helps isolate the electrode assembly from the microprocessor assembly. Also illustrated is the hydrophobic, oxygen permeable membrane means 34 preferably filling the space between the first membrane means 26 and the housing 10 except in the area of the first working electrode (not illustrated). FIG. 2 shows a feed-through 57 connecting the counter electrode of the electrode assemble to the microprocessor assembly. It will be appreciated by those of skill in the art that the illustrated feed-through 57 is representative of the feed-throughs connecting each electrode in the electrode assembly with the microprocessor assembly.

Figure 3:
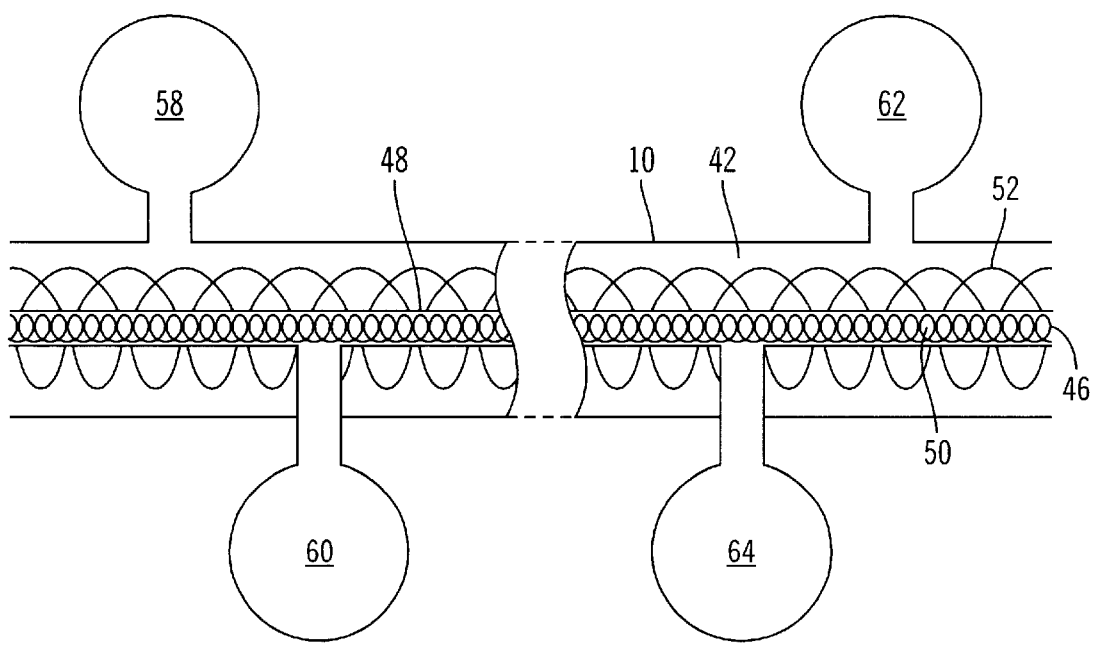
FIG. 3 is a partial side view of an alternative embodiment of the monitoring system showing primary and secondary reservoir bulbs for both the electrolyte and enzyme solutions as described herein.

A further alternative embodiment of the implantable monitoring system contemplated herein is illustrated in FIG. 3. In this embodiment, at least one (primary) enzyme reservoir bulb 58 and at least one (primary) electrolyte reservoir bulb 60 are associated, respectively, with the enzyme reservoir 42 and the electrolyte reservoir 50. The reservoir bulbs 58, 60 are in fluid communication with their respective reservoirs 42, 50. During implantation of the monitoring system, the reservoir bulbs 58, 60 are preferably positioned near the surface of the skin. Such positioning permits the physician or other medical personnel or patient to access the reservoir bulbs 58, 60 using a hypodermic needle; thereby permitting removal/addition of the enzyme and electrolyte solutions contained therein.

In a still further embodiment, a secondary enzyme reservoir bulb 62 and secondary electrolyte reservoir bulb 64 are added to the monitoring system, preferably some distance from the primary enzyme reservoir bulb 58 and primary electrolyte reservoir bulb 60; for example on the opposite side of the sensor assemblies. As with the primary reservoir bulbs 58, 60, the secondary reservoir bulbs 62, 64 are preferably implanted near the skin surface for easy access via needle insertion. In this further embodiment, fresh enzyme and/or electrolyte solutions may be injected or pumped into the primary reservoir bulbs while "old" enzyme and/or electrolyte solutions are removed from the secondary reservoir bulbs at the same rate; thereby permitting a flushing or complete refreshment of the entire system without the need for explantation.

Figure 4:
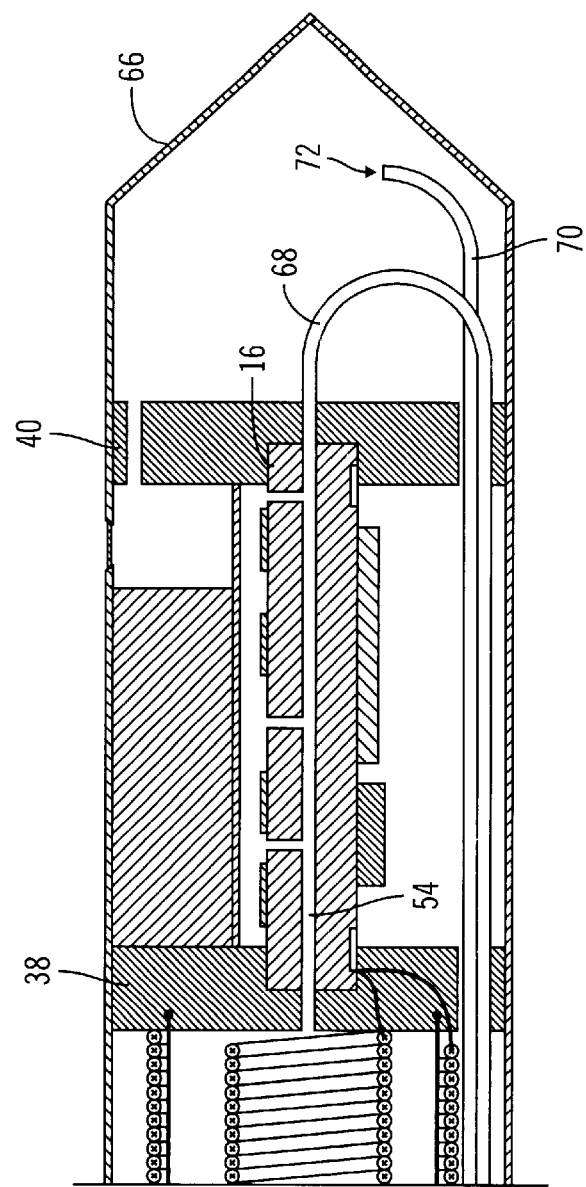
FIG. 4 is a partial side view of an alternative embodiment of the primary and secondary reservoir bulbs illustrated in FIG. 3, showing the enzyme and electrolyte return tubes as described herein.
Figure 4:
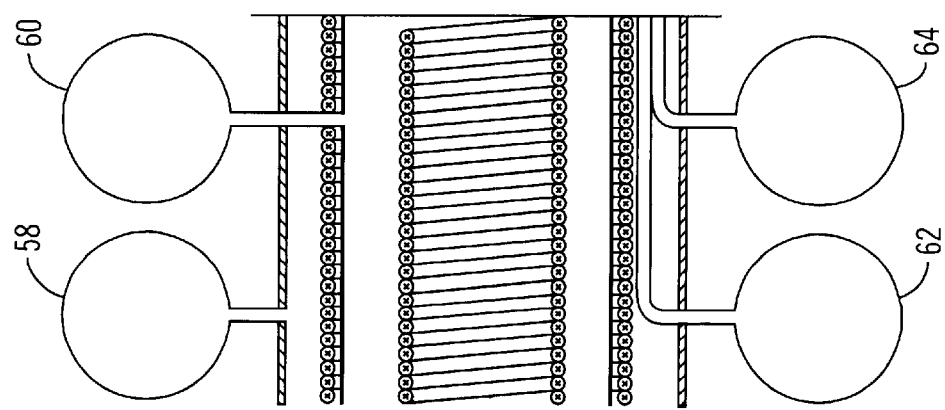

Instead of positioning the primary and secondary reservoir bulbs at opposite ends of the monitoring system, they may be positioned near each other and "return" tubes employed within the system to allow the enzyme and electrolyte solutions to return from the distant end of the monitoring system to the secondary reservoir bulbs. FIG. 4 illustrates how such return tubes 68, 70 may be positioned within the tip 66 of the monitoring system. As illustrated, the electrolyte channel 54 passing through the substrate 16 and epoxy plug 40 is contiguous with an electrolyte return tube 68 which turns and runs the length of the monitoring system to connect to the secondary electrolyte reservoir bulb 64. Similarly, an enzyme return tube 70 is positioned such that its tip 72 is open and within the tip 66 of the monitoring system. The enzyme return tube 70 then also runs the length of the monitoring system and where it connects to the secondary enzyme reservoir bulb 62. This configuration permits all four reservoir bulbs 58, 60, 62, 64 to be in close proximity to one another and to the skin surface, thereby permitting easy access for replacement of the solutions contained therein.

Alternative embodiments to the specific embodiments described herein will be readily appreciated by those of skill in the art. For example, the number and type of electrodes bonded to the substrate may vary, such as where only one working electrode is required because the substance of interest or a stoichiometrically related substance is directly measured by that electrode, eliminating the need for a second working electrode.

Further, it will be appreciated that the monitoring system may be modified to measure substances in addition to and/or other than glucose. For the purpose of measuring more than one body substance, the modifications could include use of additional enzyme chambers, enzyme channels, enzyme reservoirs and working electrodes associated with a single substrate or separate sensor assemblies for each substance to be measured. Alternatively, where neither the substances to be measured nor the reagents and products of their enzymatic reactions interfere with the measurement of the other substances, then the different enzymes may be contained within the same solution and on the same or different microspheres.

While the invention herein disclosed has been described by means of specific embodiments, numerous modifications and variations could be made thereto by those skilled in the art without departing from the scope of the invention set forth in the claims.

What is claimed is:

1. An implantable monitoring system comprising an enzyme solution and means, within the monitoring system, for replenishing the enzyme solution,
wherein the enzyme solution moves freely within the means for replenishing the enzyme solution, the enzyme solution moving through a channel on a substrate.

2. An implantable monitoring system comprising an electrode assembly bathed in an electrolyte solution and means, within the monitoring system, for replenishing the electrolyte solution.

3. An implantable monitoring system comprising:
an enzyme chamber;
an enzyme reservoir in fluid communication with the enzyme chamber; and
an enzyme solution within the enzyme chamber and enzyme reservoir,
wherein the enzyme solution moves freely between the enzyme chamber and enzyme reservoir, the enzyme solution moving through a channel on a substrate.

4. An implantable monitoring system comprising:
an electrolyte chamber;
an electrolyte reservoir in fluid communication with the electrolyte chamber; and
an electrolyte solution within the electrolyte chamber and the electrolyte reservoir.

5. An implantable monitoring system comprising:
an electrolyte chamber;
an electrolyte solution within the electrolyte chamber;
an electrolyte reservoir in fluid communication with the electrode chamber;
an enzyme chamber proximate the electrolyte chamber;
an enzyme solution within the enzyme chamber; and
an enzyme reservoir in fluid communication with the enzyme chamber.

6. An implantable monitoring system for determining the in vivo concentration of at least one prescribed substance, the system comprising:
a housing, at least a portion of which is permeable to the at least one prescribed substance;
an enzyme chamber within the housing;
an enzyme reservoir in fluid communication with the enzyme chamber;
and an enzyme solution contained within the enzyme chamber and enzyme reservoir,
wherein the enzyme solution moves freely between the enzyme chamber and enzyme reservoir, the enzyme solution moving through a channel on a substrate.

7. The implantable monitoring system of claim 6, further comprising:
an electrolyte chamber within the housing;
an electrode assembly within the electrolyte chamber;
an electrolyte reservoir in fluid communication with the electrolyte chamber; and
an electrolyte solution contained within the electrolyte chamber and electrolyte reservoir.

8. An implantable monitoring system for determining the in vivo concentration of at least one prescribed substance, the system comprising:
a housing, at least a portion of which is permeable to the at least one prescribed substance;
a substrate within the housing;
an electrode assembly affixed to the substrate and having an active surface;
an electrolyte chamber surrounding the active surface of the electrode assembly;
an electrolyte reservoir in fluid communication with the electrolyte chamber; and
an electrolyte solution contained within the electrolyte chamber and electrolyte reservoir.

9. An implantable monitoring system according to claim 8, further comprising:
an opening within the housing,
a membrane covering the opening, said membrane being permeable to the at least one prescribed substance;
an enzyme chamber within said housing and adjacent to the opening therein;
an enzyme reservoir in fluid communication with the enzyme chamber; and
an enzyme solution located within said enzyme reservoir.

10. The implantable monitoring system of claim 9, wherein the enzyme solution comprises microspheres associated with a prescribed enzyme.

11. The implantable monitoring system of claim 9, further comprising:
a microprocessor assembly hermetically associated with the substrate and in electrical communication with the electrode assembly; and
a lead system in electrical communication with the microprocessor assembly.

12. The implantable monitoring system of claim 11, wherein the housing is oxygen permeable and glucose impermeable.

13. The implantable monitoring system of claim 12, wherein the at least one prescribed substance is glucose and the enzyme solution comprises glucose oxidase.

14. The implantable monitoring system of claim 11, wherein the electrolyte reservoir and enzyme reservoir are coaxial and the lead system comprises a first lead located within the electrolyte reservoir and a second lead, coaxial with said first lead, and located within the enzyme reservoir.

15. The implantable monitoring system of claim 11, further comprising securing means, attached to said substrate, wherein the securing means serves to hold said substrate in a preselected position within said housing.

16. The implantable monitoring system of claim 15, wherein said securing means comprise at least two epoxy plugs.

17. The implantable monitoring system of claim 11, further comprising an enzyme reservoir bulb attached in fluid communication with the enzyme reservoir and extending beyond the housing such that, upon implantation, the enzyme reservoir bulb may be positioned proximate the patient's skin surface, thereby providing a point of ready access to the enzyme solution.

18. The implantable monitoring system of claim 17, further comprising an electrolyte reservoir bulb attached in fluid communication with said electrolyte reservoir and extending beyond said housing such that, upon implantation, said electrolyte reservoir bulb may be positioned proximate the patient's skin surface, thereby providing a point of ready access to the electrolyte solution.

19. The implantable monitoring system of claim 18, further comprising a second enzyme reservoir bulb and a second electrolyte reservoir bulb.

20. An implantable enzyme-based monitoring system wherein the enzyme is immobilized by microspheres.

21. A monitoring system adapted for implantation into a patient to measure the in vivo concentration of one or more prescribed substances and to measure the in vivo background concentration of oxygen, the sensor assembly comprising:

a substrate;

a first working electrode bonded to the substrate;

a reference electrode bonded to the substrate;

a collector electrode bonded to the substrate;

means for making electrical contact with the first working electrode, reference electrode, and collector electrode;

a layer of insulation deposited on the substrate and means for making electrical contact so as to be interspersed between the electrodes bonded to the substrate, the active surface of each of the electrodes being exposed through the layer of insulation, whereby the first working electrode, reference electrode and collector electrode are all electrically isolated from each other on the substrate;

first membrane means covering the electrodes and affixed to the substrate, thereby defining an electrolyte chamber;

an electrolyte solution held within the electrolyte chamber, the electrolyte solution being in contact with the electrodes bonded to the substrate;

a housing surrounding the first membrane means and the substrate, the housing having an opening therein above the active surface of the first working electrode;

second membrane means covering the opening in the housing, the second membrane means being permeable to the one or more prescribed substances to be measured;

first and second securing means for securing the substrate within the housing, the first and second securing means being positioned at opposite ends of the substrate such that a first pocket is formed by the housing, the first membrane means and the first and second securing means;

hydrophobic membrane means within the pocket and above the active surface of the second working electrode, the hydrophobic membrane means filling the portion of the pocket above the second electrode such that the portion of the pocket, above the active surface of the first working electrode, forms an enzyme chamber;

a prescribed enzyme solution contained within the enzyme chamber;

an enzyme reservoir within the housing;

an enzyme channel in fluid communication with the enzyme reservoir and the enzyme chamber;

an electrolyte reservoir within the housing and isolated from the enzyme reservoir, the electrolyte reservoir containing an electrolyte solution;

an electrolyte channel in fluid communication with the electrolyte reservoir and the electrolyte chamber; and means for applying a prescribed reference voltage between the collector electrode and the reference electrode, and between the first and second working electrodes and reference electrode, and for measuring the electrical current that flows from the first and second working electrodes, whereby, after implantation, internal oxygen may penetrate the housing, the hydrophobic membrane means and the first membrane means and alter the current flowing through the second working electrode, thereby providing a measurement of the in vivo background concentration of oxygen; and whereby, after implantation, the one or more prescribed substances to be measured may penetrate into the enzyme chamber through the second membrane means, react, in the presence of the prescribed enzyme, with oxygen that has penetrated into the enzyme chamber, such that products or reactants then penetrate the first membrane means and alter the current flowing through the first working electrode thereby providing a measurement of the concentrations of the one or more prescribed substances.

22. The implantable monitoring system of claim 21, further comprising a microprocessor assembly, hermetically bonded to the substrate.

23. The implantable monitoring system of claim 21, wherein the securing means are epoxy plugs.

24. The implantable monitoring system of claim 21, wherein the prescribed enzyme solution comprises microspheres in association with a prescribed enzyme.

25. The implantable monitoring system of claim 24, wherein the prescribed enzyme is glucose oxidase.

26. In an implantable monitoring system employing an enzyme solution, a method of extending the life of the system, comprising providing means, within the system, to replenish the enzyme solution, wherein the enzyme solution moves freely within the means for replenishing the enzyme solution, the enzyme solution moving through a channel on a substrate.

27. In an implantable monitoring system having an electrode assembly bathed in an electrolyte solution, a method of extending the life of the system, comprising providing means, within the system, to replenish the electrolyte solution.

28. An implantable monitoring system comprising a fluid solution that is altered by operation of the monitoring system and means, within the monitoring system, for replacing the altered fluid solution with unaltered fluid solution, wherein the fluid solution moves freely within the means for replacing the altered fluid solution with unaltered fluid solution, the enzyme solution moving through a channel on a substrate.

29. An implantable monitoring system according to claim 28 wherein the means for replacing the altered fluid solution comprises a reservoir system.

30. An implantable monitoring system according to claim 29 wherein the fluid solution comprises an enzyme solution.

31. An implantable monitoring system according to claim 29 wherein the fluid solution comprises an electrolyte solution.

32. An implantable monitoring system according to claim 29 comprising two fluid solutions, one of which is an enzyme solution and the other of which is an electrolyte solution.

* * * * *

UNITED STATES PATENT AND TRADEMARK OFFICE
CERTIFICATE OF CORRECTION

PATENT NO.    : 6,512,939 B1
DATED         : January 28, 2003
INVENTOR(S)   : Colvin, Michael S. et al.

It is certified that error appears in the above-identified patent and that said Letters Patent is hereby corrected as shown below:

<u>Title page,</u>
Item [73], should read -- [73] Assignee: Alfred E. Mann Foundation, Sylmar, CA --

Signed and Sealed this

Ninth Day of March, 2004

JON W. DUDAS
*Acting Director of the United States Patent and Trademark Office*